US006649579B2

(12) United States Patent
Denton

(10) Patent No.: US 6,649,579 B2
(45) Date of Patent: Nov. 18, 2003

(54) SOY BASED HAND CLEANER AND METHOD OF USE

(75) Inventor: Robert Denton, Delray Beach, FL (US)

(73) Assignee: Soy Technologies, LLC, Delray Beach, FL (US)

( * ) Notice: Subject to any disclaimer, the term of this patent is extended or adjusted under 35 U.S.C. 154(b) by 0 days.

(21) Appl. No.: 10/328,590

(22) Filed: Dec. 23, 2002

(65) Prior Publication Data

US 2003/0125223 A1 Jul. 3, 2003

Related U.S. Application Data

(60) Provisional application No. 60/346,472, filed on Dec. 29, 2001.

(51) Int. Cl.$^7$ ............................................... A61K 7/50
(52) U.S. Cl. ....................... 510/138; 510/130; 510/137; 510/159; 510/422; 510/427; 510/499; 510/491; 510/501; 510/525; 510/506
(58) Field of Search ............................... 510/130, 137, 510/138, 159, 422, 427, 491, 499, 501, 505, 506

(56) References Cited

U.S. PATENT DOCUMENTS

| 6,281,189 B1 | 8/2001 | Heimann et al. | |
| 2002/0111284 A1 * | 8/2002 | Machac, Jr. et al. | ........ 510/245 |
| 2003/0083212 A1 * | 5/2003 | Willard et al. | .............. 510/137 |

OTHER PUBLICATIONS

Bill Williams, Methyl Soyate Shows Promise As Natural Solvent, Feedstocks, May 1998, pp. 1–2, 3–2, United Soybean Board, Kansas City, MO.

* cited by examiner

*Primary Examiner*—Necholus Ogden
(74) *Attorney, Agent, or Firm*—Stockwell & Associates; Thomas P. Goodness, Esq.

(57) ABSTRACT

A composition for cleaning hands is composed of methyl soyate, a surfactant, an emulsifier, an emollient, a wetting agent, a pH-modifying agent, water and optionally other ingredients. The composition lacks d-limonene. Hands are cleaned by applying the composition to the hands, rubbing the composition over the soiled region, and removing the composition by wiping.

38 Claims, No Drawings

SOY BASED HAND CLEANER AND METHOD OF USE

CROSS-REFERENCES TO RELATED APPLICATIONS

This application claims the benefit of U.S. Provisional Application Ser. No. 60/346,472, filed Dec. 29, 2001, the contents of which is incorporated herein by reference in its entirety.

STATEMENT REGARDING FEDERALLY SPONSORED RESEARCH OR DEVELOPMENT

Not Applicable

FIELD OF THE INVENTION

The present invention relates generally to hand cleaners. More particularly, the present invention is directed to a hand cleaner comprising, inter alia, methyl soyate.

BACKGROUND OF THE INVENTION

There has been a trend in the manufacture of personal care products to use ingredients that are environmentally safe and biodegradable. As a consequence, D-limonene, a terpene generally derived from the distilled rind oils of citrus fruits has become a popular constituent in hand cleaners, such as those manufactured under the trademarks DL, PERMATEX, FAST ORANGE by Loctite Corporation, Newington, Conn.

D-limonene is desirable as a cleaner in that it is a strong, biodegradable solvent. However, D-limonene has certain properties that are not desirable in a hand cleaner. Because D-limonene is a strong solvent, excess contact with the skin can cause drying, defatting & dermatitis of skin. In addition, the strong citrus odor of D-limonene competes with the scent of perfumes that may be added to impart other pleasant odors. In addition, D-limonene is not as environmentally friendly as once thought. The Environmental Protection Agency has identified D-limonene as a Volatile Organic Compound (VOC), which contributes to the formation of ozone.

It would be desirable to formulate a hand cleaner that is non-irritating to the skin, amenable to the addition of perfumes and environmentally friendly.

SUMMARY OF THE INVENTION

Accordant with the present invention, a formula for a hand cleaner that is non-irritating to the skin, amenable to the addition of perfumes and environmentally friendly surprisingly has been discovered. The hand cleaner comprises methyl soyate, a surfactant, an emulsifier, an emollient, a wetting agent, a pH-modifying agent, water, and optionally, fragrances, colorants, preservatives or aloe vera. The hand cleaner does not contain D-limonene. The inventive formulation is particularly useful for cleaning and conditioning a person's hands.

DETAILED DESCRIPTION OF THE PREFERRED EMBODIMENT

The formulation according to the present inventor consists of a combination of methyl soyate, nonoxynol-9, PEG-75 lanolin, DMDM hydantoin, oleic acid, triethanolamine, aloe vera and water. The hand cleaner formulation does not contain D-limonene.

The inventive formula contains Methyl soyate in an amount of about 5 to about 50 percent by weight, based on the total weight of the formula. Methyl soyate is a methyl ester formed by reacting methanol with soybean oil in the presence of a catalyst. Methyl soyate is preferable to d-limonene as a solvent for a hand cleaner for several reasons. Methyl soyate is a milder solvent, and even prolonged contact with the skin is unlikely to cause drying, defatting and dermatitis of skin. To the contrary, the residue from a methyl soyate hand cleaner replenishes the skin with natural soy oil. Methyl soyate has a mild odor that will not interfere with most perfumes. Methyl soyate is not a VOC, and therefore more environmentally friendly that D-limonene.

Nonoxynol-9 is present as a non-ionic surfactant, acting as a wetting agent, detergent and emulsifier in the hand cleaner according to the present invention. In the preferred embodiment, the formula contains Nonoxynol-9 in amounts ranging from about 10 to about 14 weight percent, based on the total weight of the formula. Other surfactants that may be used instead in like amounts include, but are not limited to, sodium cocoyl isethionate, sodium dodecyl benzene sulfonate, sodium methyl oleoyl taurate, sodium lauryl sulfoacetate, sodium lauryl sulfate, sodium $C_{14-16}$ olefin sulfonate, disodium lauryl sulfosuccinate, cocamidopropyl betaine, lauramide MEA, sucrose stearate, cetyl alcohol, laureth-3, polysorbate-85, sorbitan monolaurate, PEG-30 Castor Oil, PEG-6 cocamide, and distearyl dimethyl ammonium chloride.

Cocamide-DEA is present as an emulsifier. Preferably, the formula contains Cocamide-DEA in amounts ranging from about 4 to about 10 weight percent, based on the total weight of the formula. Alternatively, other alkylamides may be substituted for Cocamide-DEA in like amounts.

PEG-75 lanolin is present in the inventive formulation as an emollient and emulsifier. Preferably, the formula contains PEG-75 lanolin in amounts from about 0.50 to about 3.50 weight percent, based on the total weight of the formula. Other emollients that may be substituted for PEG-75 lanolin in like amounts include, but are not limited to, dimethicone, cyclomethicone, lanolin oil, lanolin fatty acid, lanolin alcohol, acetylated lanolin alcohol, acetylated alkoxylated lanolin such as laneth-9 acetate and laneth-10 acetate, alkoxylated lanolin having about 30 to about 75 moles of ethylene oxide or propylene oxide such as PEG-16 lanolin, PEG-27 lanolin, PEG-40 lanolin, PPG-12–PEG-50 lanolin, long chain esters such as cetyl acetate, stearyl acetate, oleyl acetate, lauryl lactate, myristyl lactate, cetyl lactate, stearyl lactate, decyl neopentanoate, decyl oleate, isopropyl myristate, lauryl myristate, myristyl myristate, myreth-3-myristate, palmityl myristate, stearyl myristate, isopropyl palmitate, octyl palmitate, 2-ethylhexyl palmitate, lauryl palmitate, myristyl palmitate, palmityl palmitate, stearyl palmitate, butyl stearate, myristyl stearate, palmityl stearate, isocetyl stearate, isostearyl isostearate, myristyl alcohol, cetyl alcohol, isocetyl alcohol, stearyl alcohol, oleyl alcohol, dioctyl succinate, didecyl succinate, caprylic/capric triglycerides, ethoxylated cholesterol, PEG-16 soya sterol, and mixtures thereof.

Triethanolamine is present in the inventive formulation as a wetting agent, to emulsify oily ingredients and increase their retention and absorption into the skin, thus acting as a moisturizer. Triethanolamine also acts as a neutralizer. Preferably, the formula contains triethanolamine in amounts from about 0.30 to about 1.30 weight percent, based on the total weight of the formula. Optionally, other alkaline neutralizers such as monoethanolamine may be substituted in like amounts. DMDM Hydantoin is a well-known preservative used in the present formulation. Other preservatives may be used. Preferably, the amount of DMDM Hydantoin is about 0.5 to about 2 weight percent, based on the total weight of the formula.

Oleic Acid is present in the inventive formulation to provide pH balance. Typically, the formula contains oleic acid in amounts from about 1.5 to about 4.5 weight percent, based on the total weight of the formula. The preferred pH is in the range of 5.0 to 8.0; more preferably, the pH is in the range of 6.5 to 7.5. Although Oleic Acid is used in the present formulation, other compounds such as benzoic acid, acetic acid, formic acid, citric acid, and phosphoric acid are also suitable and may be substituted for Oleic Acid in amounts necessary to produce a pH in the preferred range. Oleic Acid also acts as an anti-oxidant.

The hand cleaner herein described may optionally contain Aloe Vera, to protect the user's hands when using the cleaning agent, and reduce the risk of any irritation to the user's skin. By way of example, Aloe Vera gel can be added to the formula in amounts from zero to about 25 weight percent based on the total weight of the formula.

The hand cleaner herein described may optionally contain fragrance, in amounts from about zero to about 5 percent based on the total weight of the formula.

Water is added to the hand cleaner of the present invention to make up the balance of the weight of the hand cleaner, and may be provided in an amount from about 15% to about 25% by weight, based on the total weight of the formula.

The aforementioned ingredients may be combined and mixed in conventional high-shear mixing equipment, to form a hand cleaner, according to the present invention.

EXAMPLE

Methyl Soyate 34%
Deionized Water 22%
Aloe Vera Gel 20%
Nonoxynol-9 12%
Cocamide-DEA 6%
Oleic Acid 3%
PEG-75 Lanolin 2%
Triethanolamine 0.5%
DMDM Hydantoin 0.5%

Ingredients are combined, heated to 160 degrees and mixed until homogeneous. The mixture is then cooled to room temperature. If desired, fragrance and antioxidant may be added.

To clean the hands, the composition is applied to the hands or portions thereof. The amount of the composition applied is proportional to the surface area being cleaned and the degree to which the hands are soiled. After the composition is applied, it is worked over the portion of the hands to be cleaned by rubbing. More of the hand cleaner composition is added as necessary to fully clean the hands. After the hands are sufficiently clean, the composition is wiped from the hands.

In accordance with the provisions of the patent statutes, the present invention has been described in what is considered to represent its preferred embodiment. However, it should be understood that the invention can be practiced otherwise than as specifically illustrated and described without departing from its spirit or scope.

I claim:

1. A composition for cleaning hands comprising methyl soyate, a surfactant, an emulsifier, an emollient, a wetting agent, a pH-modifying agent, and water, and does not comprise d-limonene.

2. A composition as in claim 1 wherein said composition further comprises an anti-oxidant.

3. A composition as in claim 2 wherein said anti-oxidant is oleic acid.

4. A composition as in claim 1 wherein said surfactant is selected from the group consisting of sodium cocoyl isethionate, sodium dodecyl benzene sulfonate, sodium methyl oleoyl taurate, sodium lauryl sulfoacetate, sodium lauryl sulfate, sodium $C_{14-16}$ olefin sulfonate, disodium lauryl sulfosuccinate, cocamidopropyl betaine, lauramide MEA, sucrose stearate, cetyl alcohol, laureth-3, polysorbate-85, sorbitan monolaurate, PEG-30 Castor Oil, PEG-6 cocamide, distearyl dimethyl ammonium chloride, Nonoxynol-9, and combinations thereof.

5. A composition as in claim 1 wherein said surfactant is nonoxynol-9.

6. A composition as in claim 1 wherein said surfactant is present in the range of from about 10 to about 14 weight percent, based on the total weight of the composition.

7. A composition as in claim 1 wherein said emulsifier is an alkylamide.

8. A composition as in claim 1 wherein said emulsifier is cocamide-DEA.

9. A composition as in claim 1 wherein said emulsifier is present in the range of from about 4 to about 10 weight percent, based on the total weight of the composition.

10. A composition as in claim 1 wherein said emollient is selected from the group consisting of dimethicone, cyclomethicone, lanolin oil, lanolin fatty acid, lanolin alcohol, acetylated lanolin alcohol, acetylated alkoxylated lanolin such as laneth-9 acetate and laneth-10 acetate, alkoxylated lanolin having about 30 to about 75 moles of ethylene oxide or propylene oxide such as PEG-16 lanolin, PEG-27 lanolin, PEG-40 lanolin, PPG-12–PEG-50 lanolin, long chain esters such as cetyl acetate, stearyl acetate, oleyl acetate, lauryl lactate, myristyl lactate, cetyl lactate, stearyl lactate, decyl neopentanoate, decyl oleate, isopropyl myristate, lauryl myristate, myristyl myristate, myreth-3-myristate, palmityl myristate, stearyl myristate, isopropyl palmitate, octyl palmitate, 2-ethylhexyl palmitate, lauryl palmitate, myristyl palmitate, palmityl palmitate, stearyl palmitate, butyl stearate, myristyl stearate, palmityl stearate, isocetyl stearate, isostearyl isostearate, myristyl alcohol, cetyl alcohol, isocetyl alcohol, stearyl alcohol, oleyl alcohol, dioctyl succinate, didecyl succinate, caprylic/capric triglycerides, ethoxylated cholesterol, PEG-16 soya sterol, PEG-75 lanolin and combinations thereof.

11. A composition as in claim 1 wherein said emollient is PEG-75 lanolin.

12. A composition as in claim 1 wherein said emollient is present in the range of from about 0.50 to about 3.50 weight percent, based on the total weight of the composition.

13. A composition as in claim 1 wherein said wetting agent is selected from the group consisting of triethanolamine, or monoethanolamine, and combinations thereof.

14. A composition as in claim 1 wherein said wetting agent is triethanolamine.

15. A composition as in claim 1 wherein said wetting agent is present in the range of from about 1.5 to about 4.5 weight percent, based on the total weight of the composition.

16. A composition as in claim 1 wherein said pH-modifying agent is selected from the group consisting of benzoic acid, acetic acid, formic acid, citric acid, phosphoric acid, oleic acid, and combinations thereof.

17. A composition as in claim 1 wherein said pH-modifying agent is oleic acid.

18. A composition as in claim 1 wherein said pH-modifying agent is present in the range of from about from about about 0.30 to about 1.30 weight percent, based on the total weight of the composition.

19. A composition as in claim 1 wherein said pH-modifying agent is present in an amount sufficient to cause the pH to fall within the range of 6.5 to 7.5.

20. A composition as in claim 1 wherein said pH-modifying agent is present in an amount sufficient to cause the pH to fall within the range of 5.0 to 8.0.

21. A method of cleaning hands comprising applying a composition comprising methyl soyate, a surfactant, an emulsifier, an emollient, a wetting agent, a pH-modifying agent, water and said composition not comprising d-limonene to the hands, rubbing the composition over the soiled region of the hands and removing the composition from the hands by wiping.

22. A method as in claim 21 wherein wherein said surfactant is selected from the group consisting of sodium cocoyl isethionate, sodium dodecyl benzene sulfonate, sodium methyl oleoyl taurate, sodium lauryl sulfoacetate, sodium lauryl sulfate, sodium $C_{14-16}$ olefin sulfonate, disodium lauryl sulfosuccinate, cocamidopropyl betaine, lauramide MEA, sucrose stearate, cetyl alcohol, laureth-3, polysorbate-85, sorbitan monolaurate, PEG-30 Castor Oil, PEG-6 cocamide, distearyl dimethyl ammonium chloride, Nonoxynol-9, and combinations thereof.

23. A method as in claim 21 wherein said surfactant is nonoxynol-9.

24. A method as in claim 21 wherein said surfactant is present in the range of from about 10 to about 14 weight percent, based on the total weight of the composition.

25. A method as in claim 21 wherein said emulsifier is an alkylamide.

26. A method as in claim 21 wherein said emulsifier is cocamide-DEA.

27. A method as in claim 21 wherein said emulsifier is present in the range of from about 4 to about 10 weight percent, based on the total weight of the composition.

28. A method as in claim 21 wherein said emollient is selected from the group consisting of dimethicone, cyclomethicone, lanolin oil, lanolin fatty acid, lanolin alcohol, acetylated lanolin alcohol, acetylated alkoxylated lanolin such as laneth-9 acetate and laneth-10 acetate, alkoxylated lanolin having about 30 to about 75 moles of ethylene oxide or propylene oxide such as PEG-16 lanolin, PEG-27 lanolin, PEG-40 lanolin, PPG-12–PEG-50 lanolin, long chain esters such as cetyl acetate, stearyl acetate, oleyl acetate, lauryl lactate, myristyl lactate, cetyl lactate, stearyl lactate, decyl neopentanoate, decyl oleate, isopropyl myristate, lauryl myristate, myristyl myristate, myreth-3-myristate, palmityl myristate, stearyl myristate, isopropyl palmitate, octyl palmitate, 2-ethylhexyl palmitate, lauryl palmitate, myristyl palmitate, palmityl palmitate, stearyl palmitate, butyl stearate, myristyl stearate, palmityl stearate, isocetyl stearate, isostearyl isostearate, myristyl alcohol, cetyl alcohol, isocetyl alcohol, stearyl alcohol, oleyl alcohol, dioctyl succinate, didecyl succinate, caprylic/capric triglycerides, ethoxylated cholesterol, PEG-16 soya sterol, PEG-75 lanolin and combinations thereof.

29. A method as in claim 21 wherein said emollient is PEG-75 lanolin.

30. A method as in claim 21 wherein said emollient is present in the range of from about 0.50 to about 3.50 weight percent, based on the total weight of the composition.

31. A method as in claim 21 wherein said wetting agent is selected from the group consisting of triethanolamine, or monoethanolamine, and combinations thereof.

32. A method as in claim 21 wherein said wetting agent is triethanolamine.

33. A method as in claim 21 wherein said wetting agent is present in the range of from about 1.5 to about 4.5 weight percent, based on the total weight of the composition.

34. A method as in claim 21 wherein said pH-modifying agent is selected from the group consisting of benzoic acid, acetic acid, formic acid, citric acid, phosphoric acid, oleic acid, and combinations thereof.

35. A method as in claim 21 wherein said pH-modifying agent is oleic acid.

36. A method as in claim 21 wherein said pH-modifying agent is present in the range of from about from about about 0.30 to about 1.30 weight percent, based on the total weight of the composition.

37. A method as in claim 21 wherein said pH-modifying agent is present in an amount sufficient to cause the pH to fall within the range of 6.5 to 7.5.

38. A method as in claim 21 wherein said pH-modifying agent is present in an amount sufficient to cause the pH to fall within the range of 5.0 to 8.0.

* * * * *